«12» United States Patent
Geremia et al.

(10) Patent No.: US 6,417,354 B1
(45) Date of Patent: *Jul. 9, 2002

(54) 1,4,7,10-TETRAAZACYCLODODECANE-1,4-DIACETIC ACID

(75) Inventors: Renato Geremia; Marcella Murru; Giorgio Ripa; Vittorio Valle, all of Milan (IT)

(73) Assignee: Dibra S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/582,578

(22) PCT Filed: Dec. 21, 1998

(86) PCT No.: PCT/EP98/08364

§ 371 (c)(1),
(2), (4) Date: Jul. 14, 2000

(87) PCT Pub. No.: WO99/35134

PCT Pub. Date: Jul. 15, 1999

(30) Foreign Application Priority Data

Dec. 30, 1997 (IT) .......................................... MI97A2895

(51) Int. Cl.⁷ .......................................... C07D 295/182
(52) U.S. Cl. ........................ 540/465; 540/472; 540/474
(58) Field of Search ................................ 540/465, 472, 540/474

(56) References Cited

U.S. PATENT DOCUMENTS 5,132,409 A * 7/1992 Felder et al. .................. 534/10
5,410,043 A * 4/1995 Platzek et al. ............... 540/465

FOREIGN PATENT DOCUMENTS

EP       0 325 762 A     2/1989
WO         95 14726 A    1/1995
WO       WO-9700087   *  3/1997
WO       WO-9736619   *  9/1997

OTHER PUBLICATIONS

Meunier et al .Canadian Journal of Chemistry 73 (1995) 685–695.*
Aime et al. Inorg. Chem. 31 (1992) 1100.*
Z. Li et al. : "Selective mono–and 1,4–di–N–alkylations of 1,4,7,10–tetraazacyclodecane" Acta Chemica Scandinavica., vol. 52, No. 10, Oct. 1998, pp. 1247–1253, XP002101578 Copenhagen DK see the whole document.

* cited by examiner

Primary Examiner—Richard L. Raymond
Assistant Examiner—Venkataraman Balasubramanian
(74) Attorney, Agent, or Firm—Nixon & Vanderhye P.C.

(57) ABSTRACT

1,4,7,10-tetraazacyclododecane-1,4-diacetic acid of formula (I):

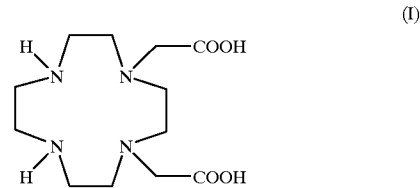

as well as its chelated complex salts with bi-valent metal ions having atomic numbers from 20 to 31, 39, 42, 43, 44, 49, or from 57 to 83, as well as their salts with anions of physiologically acceptable organic acid selected from acetate, succinate, citrate, fumarate, maleate, oxalate, or with anions of inorganic acids selected from halo acids ions. The compounds are intermediates for preparing 1,4,7,10-tetraaza-cyclododecane chelating agents.

14 Claims, No Drawings

1,4,7,10-TETRAAZACYCLODODECANE-1,4-DIACETIC ACID

The present invention relates to the novel compound, acid 1,4,7,10-tetraazacyclododecane-1,4-diacetic of formula (I), its complexes with paramagnetic metal ions and physiologically compatible salts thereof, as well as to the preparation thereof and the use thereof for the preparation of chelating agents.

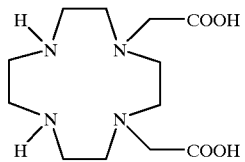

(I)

The compound of formula (I) is a novel chelating agent for bi-trivalent metal ions and is also an important intermediate for the synthesis of 1,4,7,10-tetraazacyclododecane derivatives chelating agents, functionalized at the 1-and 4-positions with the acetic residue.

The compound of formula (I) is the starting material for the synthesis of multidentate derivatives which are capable of complexing different metals, some of which have applications in the biomedical field, such as gadolinium complexes of said derivatives, which are used in diagnostic as contrast agents for the magnetic resonance technique (Magnetic Resonance Imaging, MRI).

Such complexes have been described, inter alia, in EP 325762.

Therefore, the object of the present invention is the compound of formula (I):

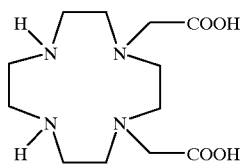

(I)

as well as its chelated complex salts with bi-trivalent metal ions having atomic number from 20 to 31, 39, 42, 43, 44, 49, or from 57 to 83, as well as their salts with anions of physiologically acceptable organic acids, selected from, for example, acetate, succinate, citrate, fumarate, maleate, oxalate, or with anions of inorganic acids such as halo acids ions, specificallychlorides, bromides, iodides.

Metal ions suitable for preparing chelated complex salts with the novel chelating agent (I) are mainly bivalent or trivalent ions of the elements having atomic number variable from 20 to 31, 39, 42, 43, 44, 49, or from 57 to 83; particularly preferred being $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $La^{(3+)}$, $Yb^{(3+)}$ or $Mn^{(2+)}$ also radioisotopes such as $^{51}Cr$, $^{67}Ga$, $^{68}Ga$, $^{111}In$, $^{99m}Tc$, $^{140}La$, $^{175}Yb$, $^{153}Sm$, $^{166}Ho$, $^{90}Y$, $^{149}Pm$, $^{177}Lu$, $^{47}Sc$, $^{142}Pr$, $^{159}Gd$, $^{212}Bi$.

The novel compounds of the present invention have a good tolerability; moreover, their water solubility and the limited osmolality of their solutions are a further advantageous characteristic which makes them particularly suitable for use in nuclear magnetic resonance.

Both soluble and less soluble compounds are useful for the oral and enteral administrations and, therefore, for the imaging of the gastronitestinal (GI) tract.

As far as the parenteral administration is concerned, the compounds are preferably formulated as a sterile aqueous solution or suspension, whose pH can range for instance from 6.0 to 8.5.

These aqueous solutions or suspensions can be administered in concentrations ranging from 0.002 to 1.0 mol.

These formulations can be lyophilized and supplied as they are for reconstitution before use.

For the GI use or for the injection in the body cavities, such agents can be formulated as a solution or suspension containing suitable additives which can control viscosity.

In the oral administration they can be formulated according to preparation methods commonly used in the pharmaceutical practice, possibly also as coated formulations, in order to get additional protection from the stomach acid pH, by preventing the release of the chelated metal ion occurring in particular at pH which are typical of gastric juices.

Other excipients, for instance sweeteners and/or flavouring agents, can also be added according to known techniques of pharmaceutical formulation.

In the diagnostic field, the chelated complex salts of this invention can be used as contrast agents, while as radiopharmaceuticals in nuclear medicine, they are useful both in the diagnostic and therapeutic sector.

In this case, however, the metal ion which is chelated is a radioisotope, for instance $^{51}Cr$, $^{67}Ga$, $^{68}Ga$, $^{111}In$, $^{99m}Tc$, $^{140}La$, $^{175}Yb$, $^{153}Sm$, $^{166}Ho$, $^{90}Y$, $^{149}Pm$, $^{177}Lu$, $^{47}Sc$, $^{142}Pr$, $^{159}Gd$ and $^{212}Bi$.

The compounds object of the present invention can optionally be chemically conjugated with suitable macromolecules or included in suitable carriers.

Preferred anions of inorganic acids suitable for salifying the chelated complex salts of the invention comprise, in particular, halo acids ions such as chlorides, bromides, iodides or other ions, such as sulfate.

Preferred anions of organic acids suitable for the above aim comprise those of the acids conventionally used in pharmaceutical technique for the salification of basic substances, such as acetate, succinate, citrate, fumarate, maleate.

Preferred amino acid anions comprise, for example, those of taurine, glycine, lysine, arginine or ornithine, or of aspartic and glutamic acids.

The chelated complex salts of compound (I) with the metal ions defined above are prepared according to procedures known in literature, by reacting compound (I) with the oxide or the halide of the selected metal ion.

More specifically, the reaction is carried out in water or in a suitable water-alcohol mixture, and the temperature can range from 25° C. to 100° C., preferably from 40° C. to 80° C.

The choice of the metal ion and of any neutralizing ion is closely related to the intended use of the complex to be prepared.

The preparation of the novel compound, manganese chelated complex of 1,4,7,10-tetraazacyclododecane-1,4-diacetic acid, which is in the neutral form and therefore does not require the formation of a physiologically compatible salt, is described in the Experimental section.

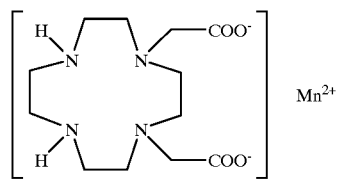

The compound of formula (I) was surprisingly prepared starting from octahydro-2a,4a,6a,8a-tetraazapentalen[1,6- cd]pentalene (CAS RN 54364-78-2) of formula (II), and from 1,2,3,4,6,7,8,9-octahydro-5H-4a,7,9a-triaza-2a-azoniacycloocta[cd] pentalene chloride of formula (IV), both obtainable according to known methods from 1,4,7,10-tetraazacyclododecane (III) (commonly named Cyclen), according to the following Scheme 1, through the formation of the novel compound of formula (V), 1,4,7,10-tetraazabicyclo[8.2.1]tridecane-13-on-4,7-diacetic acid, which is also an object of the invention:

the respective preparations of said compounds being already disclosed in U.S. Pat. No. 3,932,451 and in a paper (Richman et Simmons, Tetrahedron, 30, 1769, 1974), for the use of both of them in photography.

The compound of formula (II) is obtainable by benzene extraction from the alkalinized solution of compound (IV), which can easily be prepared in quantitative yields from 1,4,7,10-tetraazacyclododecane (commercial product, commonly named Cyclen) of formula (III), by reaction with Scheme 1

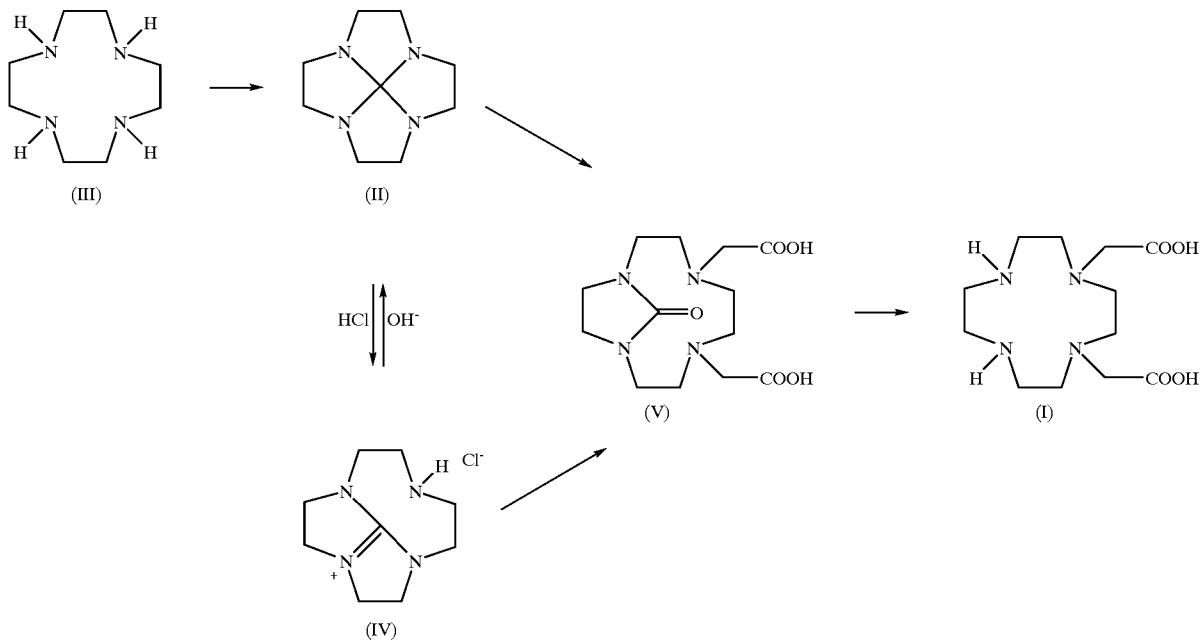

The compound of formula (II) quickly and reversibly dissociates in water to give the compound of formula (IV), ethyl orthocarbonate and an equivalent of hydrochloric acid in ethanol, as shown in the following Scheme:

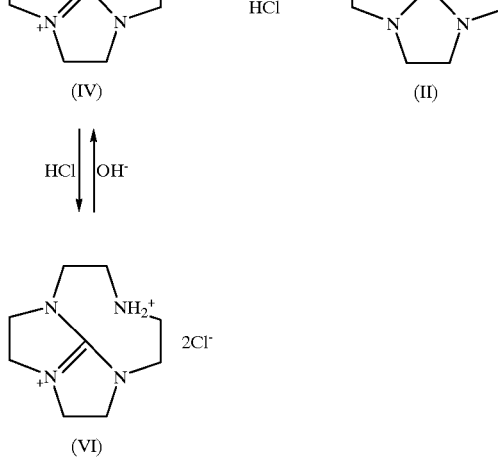

The compound of formula (IV) is in prototropic equilibrium at room temperature with compound (II) and with the dicationic compound (VI). This equilibrium is also of conformational type, thus causing the magnetic equivalence of protons of compound (II).

U.S. Pat. No. 3,932,451 discloses the preparation of these compounds starting from 2,3,5,6-tetraidro-1H-imidazo[1,2a]-imidazole, as shown in the following Scheme:

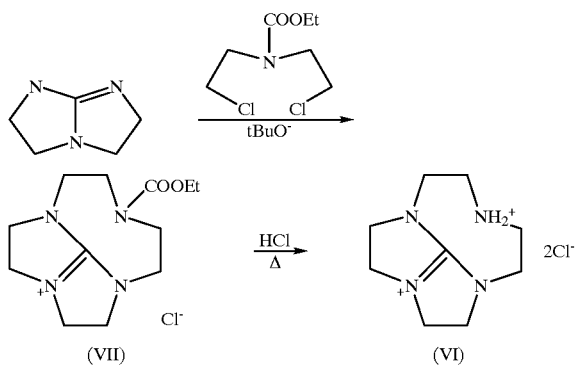

The compound of formula (II) quickly reconverts to compound (VII) by reaction with ethyl chloroformate, thus giving further structural evidences.

From such a behaviour of the compounds of formula (II) and (IV), documented in literature, no uses of these compounds as useful intermediates for the synthesis of 1,4-disubstituted 1,4,7,10-tetraazacyclododecane derivatives could be expected.

It is a further object of the invention the process for the preparation of the novel compound of formula (I), starting from known compounds of formula (II) or (IV), through the formation of the novel compound of formula (V), comprising the following steps represented in Scheme 2:

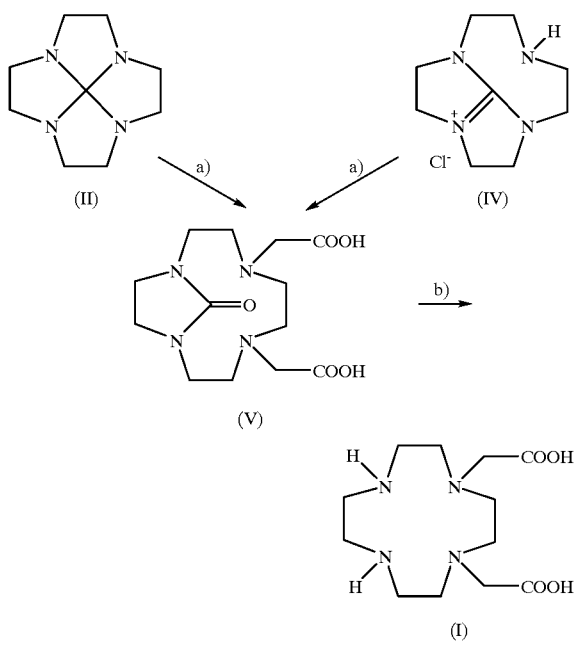

in which step a) is the alkylation reaction in basic conditions with an acetic acid reactive derivative, $XCH_2COOH$, in which X is a halogen;

step b) is the basic hydrolysis under pressure and at a temperature ranging from 150–220° C.

The alkylation conditions in step a) are conventional ones: the reaction temperature can range from 30 to 70° C.; the reaction time usually ranges from 10 to 25 hours; the basic pH ranges from 10 to 12 and is obtained by addition of a inorganic base, preferably sodium or potassium hydroxide; the amount of alkylating agent is stoichiometric or in a slight excess (up to 50%).

Preferred conditions in the presence of at least 2 mols of $BrCH_2COOH$ as alkylating agent per mol of starting product are the following: temperature 45° C.; reaction time 21 hours; pH 11.5.

Compound of formula (V) is purified by elution of the acidified final solution on a polystyrene adsorbing resin, such as XAD-1600, to remove the salts, and subsequent recovery of the desired product.

Compound (V), whose structure was confirmed by spectroscopic analysis ($^1$H-NMR, $^{13}$C-NMR, IR and MS), shows a high stability under hydrolytic conventional conditions.

It has surprisingly been found that the basic hydrolysis of this compound at high temperature and under pressure causes the loss of the carbonyl bridge, while keeping the acetic residues intact, thereby yielding simply and efficiently compound of formula (I).

The basic hydrolysis is carried out in aqueous medium at basic pH by addition of an amount of inorganic base, as defined above, corresponding to 4–7 mols per mol of compound (V) at temperatures of 150–220° C.; pressure depending of course by the selected temperature to carry out the reaction according to ideal gas law; the reaction time ranging from 15 to 30 hours.

Preferred conditions are as follows: temperature 195° C. and pressure 10 bars; 5 mols of NaOH per mol of compound (V); reaction time 22 hours.

The compound of formula (I) is in its turn a useful starting product for the synthesis of the compounds of general formula (VIII),

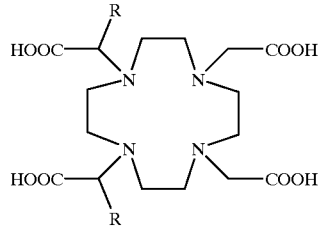

(VIII)

which are useful chelating agents of paramagnetic metal ions, for the preparation of contrast agents for magnetic resonance imaging, as described in EP 325762.

It is therefore an object of the invention the process for the preparation of compounds (VIII), starting from compound (I), by alkylation, according to known methods, with an excess of alkylating agent R—CH(X)—COY of formula (IX), optionally followed by hydrolysis of the ester groups present, as shown in the following Scheme 3:

Scheme 3

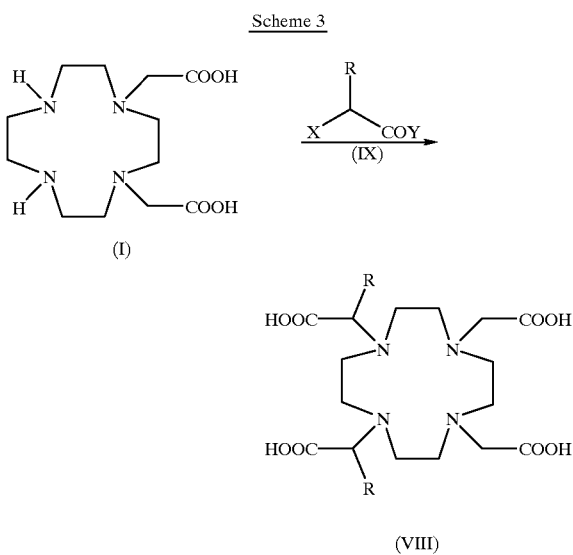

in which

R is a hydrogen atom, a straight or branched or cyclic $C_1$–$C_6$ alkyl group, unsubstituted or substituted by 1 to 10 oxygen atoms, or a $C_1$–$C_{20}$ alkyl group, optionally interrupted by a phenylene, phenylenoxy or phenylenedioxy group, in its turn substituted by a straight or branched $C_1$–$C_6$ alkyl group, unsubstituted or substituted by 1 to 7 hydroxy groups or 1 to 3 $C_1$–$C_7$ groups; the aromatic group can be unsubstituted or substituted by alkoxy groups or by halogens, carboxy, carbamoyl, alkoxycarbonyl, sulfamoyl, hydroxyalkyl, amino, acylamino, acyl, hydroxyacyl groups;

X is a halogen or a sulfonic acid reactive residue,

Y is a group —OH or —$OR_1$, wherein $R_1$ is a straight or branched $C_1$–$C_4$ alkyl group; when Y is —$OR_1$, the ester groups are subjected to a hydrolysis step, according to known methods, to obtain compounds (VIII).

The alkylating agents of formula (IX) corresponding to compound of formula (X), R—CH(X)—COOH, in which X is bromine or chlorine, are preferred; the alkylating agents of formula (XI), $XCH_2COOH$, in which R is a hydrogen atom and X is bromine or chlorine, being most preferred.

In the other cases the alkylating agent of formula (IX) can be selected from compounds that are commercially available or the preparation of which has already been described in literature (see for example WO 93/24469 or EP 325762), or from those still to synthesize, using for example known methods for the preparation of suitable precursors (for example, in case of acyl chlorides α-halogen derivatives, see: Harpp et al., J. Org. Chem., 40, 3420, 1975), and subsequent transformation into the desired product.

Preferably R can be selected from the group consisting of: H or a straight or branched alkyl group, such as a methyl, ethyl, propyl, isopropyl, butyl, isobutyl group, in its turn substituted by hydroxy groups or interrupted by oxygen atoms, as defined above.

When an aromatic group is present in R, particularly preferred are the phenyl, benzyl, phenylmethoxymethyl groups.

Particularly preferred are 3-(phenylmethoxy)propanoic acid reactive derivatives, such as 2-bromo-3-(phenylmethoxy)propanoic acid, the preparation of which is described in Grossman et al., Chem. Ber., 91, 538, 1958, and 2-chloro-3-(phenylmethoxy)propanoic acid (CAS RN 124628-32-6), prepared analogously to the brominated derivative.

On the other hand, the group $R_1$ is preferably selected from: methyl, ethyl, isopropyl, butyl, tert-butyl.

The reactive group X can be selected, by way of example, from the group consisting of halogens (Cl, Br, I), or it is a mesylate ($MeSO_2O-$), benzenesulfonyloxy ($PhSO_2O^-$), nitrobenzenesulfonyloxy ($p-NO_2PhSO_2O^-$), tosylate ($TsO^-$) or triflate ($CF_3SO_3^-$) group.

Particularly preferred are the compounds in which X is a halogen, a bromide or a chloride being most preferred.

The alkylation of compound (I), when Y is the hydroxy group, can conveniently be performed with secondary carboxylic acids reactive derivatives, such as 2-bromopropionic acid, in aqueous alkaline solution, at temperatures from 25 to 55° C.

Particularly preferred are the alkylating agents of general formula (X), in which Y is a hydroxyl group, corresponding to bromoacetic acid (commercially available product), 2-bromopropionic acid (commercially available product), 2-bromobutyric acid (commercially available product).

On the other hand, when the alkylation reaction is carried out with an ester derivative of compound (IX), the reaction solvent can suitably be selected from dipolar aprotic solvents, in particular from dimethylformamide (DMF), dimethylacetamide (DMA), dimethylsulfoxide (DMSO), acetonitrile ($CH_3CN$) and N-methylpyrrolidone, and the reaction is carried out in the presence of an organic base, preferably a tertiary aliphatic amine selected from triethylamine (TEA), diisopropylethylamine and tributylamine.

In this case it can be convenient to transform also the acid groups (—COOH) present in compound (I) into the ester groups (—$COOR_1$), in order to promote the alkylation reaction, depending on the reactivity of the alkylating agent itself.

The reaction temperature will range, in this case, from 0 to 80° C., depending on the reactivity of the selected alkylating agent.

In this case, the alkylation reaction will be followed by basic hydrolysis of the resulting diester, in conventional conditions, to obtain the desired compound of formula (VIII).

By way of example of the huge potentialities provided by this synthetic route, the synthesis of the novel compound, α,α'-bis(methyl)-1,4,7,10-tetraazacyclododecane-1,4,7,10-tetraacetic acid:

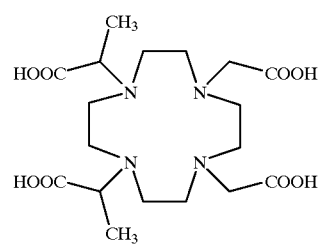

as well as that of α,α'-bis((phenylmethoxy)methyl)-4,7,10-tetraazacyclododecane-1,4,7,10-tetraacetic acid:

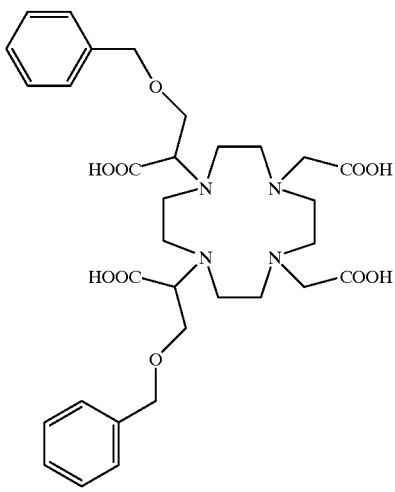

are reported in the Experimental section, in which catalytic hydrogenation, as described in example 6 of the cited Patent, leads to α,α'-bis(hydroxymethyl)-1,4,7,10-tetraazacyclododecane-1,4,7,10-tetraacetic acid.

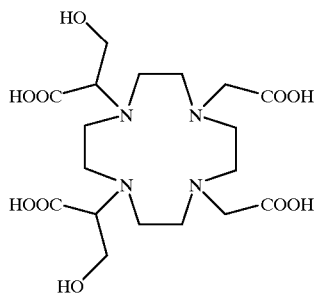

In the following, some preparation examples according to the method of the present invention are reported.

EXPERIMENTAL SECTION

Example 1

Synthesis of octahydro-2a,4a,6a,8a-tetraazapentalen[1,6-cd]pentalene

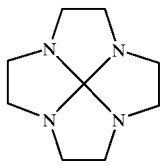

200 g of 1,4,7,10-tetraazacyclododecane (1.16 mol) are dissolved in 3 L of toluene. Water is removed by azeotropical distillation to a residual content of 0.25% (Karl Fisher). The volume of the solution is restored by adding a toluene amount corresponding to that distilled off. The solution is added with 100 mL of propionic acid (1,37 mol), at a temperature of 80° C., then heated to 90° C. adding 304 mL of ethyl orthocarbonate (1.40 mol). The solution is reacted for 22 h at 90° C., then cooled and concentrated by evaporation under vacuum, to obtain an oily residue, corresponding to 320 g of the desired product.

GC assay: 93.5% (area %)

$^1$H-NMR, $^{13}$C-NMR, IR and MS spectra are consistent with the structure.

Example 2

Synthesis of 1,4,7,10-tetraazabicyclo[8.2.1]tridecan-13-on-4,7-diacetic acid

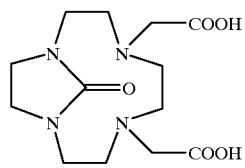

The residue obtained according to the procedure described in example 1, is dissolved in 2 L of deionized water. 2N NaOH to pH 12 and 452 g of an 80% w/w bromoacetic acid aqueous solution (2,60 mol). The mixture is heated to 45° C. and reacted at pH 11.5 (keeping this pH by gradual additions of 2N NaOH) for 21 h.

The solution is cooled, acidified with 34% HCl w/w to pH 1.1 and concentrated by evaporation under vacuum, to a weight of 2.7 kg.

The solution is percolated on 15 L of adsorbing resin XAD-1600 eluting with water. The fractions containing the useful product and free from salts are collected, combined and concentrated to dryness.

266 g (0.84 mol) of the desired product are thereby obtained.

Yield: 75% (calculated on the amount of 1,4,7,10-tetraazacyclododecane of Example 1)

$^1$H-NMR, $^{13}$C-NMR, IR and MS spectra are consistent with the structure.

Example 3

Synthesis of 1,4,7,10-tetraazacyclododecane-1,4-diacetic acid

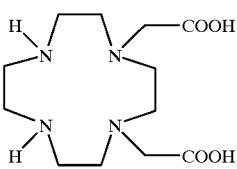

(I)

260 g of 1,4,7,10-tetraazabicyclo[8.2.1]tridecan-13-one (0.827 mol) are dissolved in 1 L of deionized water. 0.56 kg of 30% NaOH w/w are added to the solution which is placed in autoclave. The solution is left at 195° C. for 24 h, cooled, acidified to pH 4 with 34% HCl and filtered through paper.

The filtrate is percolated on 12 L of resin Relite 3ASFB, washing first with water, then eluting the product with 7 L of 1M HCl, 8 L of 0.5M HCl and 20 L of water, in this order. The fractions containing the product are combined and concentrated under vacuum to a weight of 3.5 kg. The resulting solution is percolated on a column containing 10 L of polyvinylpyridine resin, eluting with water. The fractions containing the desired product are combined and concentrated to obtain 290 g of an oily residue, which is redissolved in 1.4 L of methanol. The solution is again concentrated to dryness, to obtain 205 g of a solid that is recrystallized from the methanol/acetone mixture.

147 g of the desired product (0.81 mol) are obtained.

Yield: 61%

$^1$H-NMR $^{13}$C-NMR and MS spectra are consistent with the structure.

Example 4

Synthesis of 1,2,3,4,6,7,8,9-octahydro-5H-4a,7,9a-triaza-2a-azonia-cycloocta[cd]pentalene (CAS RN 54364-76-0) chloride

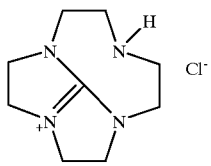

The procedure described by Richman and Simmons (Tetrahedron, 30. 1769, 1974) is followed.

50 g of 1,4,7,10-tetraazacyclododecane (0.29 mol) yield 59.5 g (0.27 mol) of the desired product (95% yield).

Example 5

Synthesis of 1,4,7,10-tetraazabicyclo[8.2.1]tridecan-13on-4,7-diacetic acid starting from 1,2,3,4,6,7,8,9-octahydro-5H-4a,7,9a-triaza-2a-azoniacycloocta[cd]pentalene chloride The product obtained according to Example 4 is dissolved in 500 g of deionized water. 2N NaOH is added to adjust to pH 12 and 106 g (0.60 mol of an 80% w/w bromoacetic acid aqueous solution are added The mixture is reacted as already described in Example 2.

63 g of the desired product (0.19 mol) are obtained.

Yield: 69%

$^1$H-NMR, $^{13}$C-NMR, IR and MS spectra are consistent with the structure.

Example 6

Synthesis of α,α'-bis(methyl)-1,4,7,10-tetraazacyclododecane-1,4,7,10-tetraacetic acid

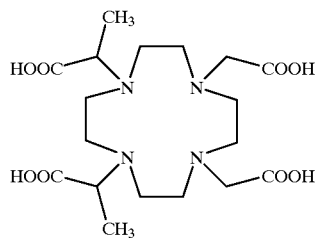

28 g (0.095 mol) of 1,4,7,10-tetraazacyclododecane-1,4-diacetic acid, prepared according to Example 3, are dissolved in 250 mL of deionized water. The solution is heated to 100° C. for 8 h, cooled to room temperature, diluted with 45 g of water and slowly added with a solution prepared dissolving 45.89 g (0.300 mol) of 2-bromopropionic acid in 40 mL of water. The mixture is reacted at a temperature of 45° C. for 25 h, keeping pH at 10.5–11 by addition of 2N NaOH. The mixture is cooled to room temperature and acidified to pH 2 with conc. hydrochloric acid. After 1 h the precipitated solid is filtered, washing with deionized water. The crude product is redissolved in 600 mL of polyvinylpyridine resin (PVP), eluting thoroughly with water. The useful fractions are combined, concentrated to dryness under vacuum and dried in static drier at 50° C. under vacuum, to obtain 35.3 g (0.080 mol) of the desired product.

Yield: 84%

$^1$H-NMR, $^{13}$C-NMR, IR and MS spectra are consistent with the structure.

Example 7

Synthesis of α4,α7-bis[(phenylmethoxy)methyl]-1,4,7,10-tetraazacyclo-dodecane-1,4,7,10-tetraacetic acid

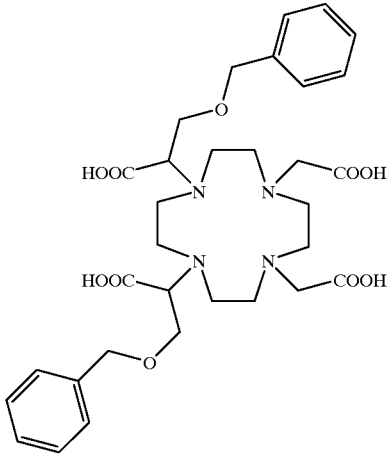

1,4,7,10-Tetraazacyclododecane-1,4-diacetic acid is reacted with 2-bromo-3-(phenylmethoxy)propanoic acid methyl ester or with 2-trifluoromethanesulfonate-2-(phenylmethoxy)propanoic acid methyl ester in DMF and in the presence of TEA. The methyl ester is hydrolysed to obtain the desired product.

$^1$H-NMR, $^{13}$C-NMR, IR and MS spectra are consistent with the structure.

Example 8

Synthesis of α1,α4-bis(hydroxymethyl)1,4,7,10-tetraazacyclodode-cane-1,4,7,10-tetraacetic acid

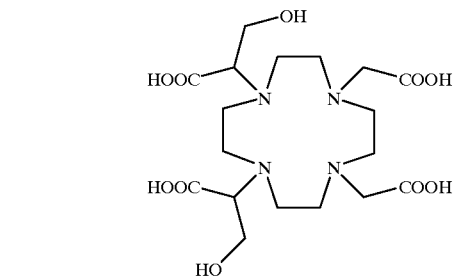

The product obtained in Example 7 is subjected to catalytic hydrogenation in water and in the presence of 5% Pd/C, to obtain, after the necessary hydrogen has been used, the desired product.

¹H-NMR, ¹³C-NMR, IR and MS spectra are consistent with the structure.

Example 9

Preparation of 1,4,7,10-tetraazacyclododecane-1,4-diacetic acid manganese chelated complex

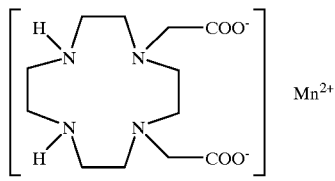

8.66 g of compound (I) prepared as described in Example 3 (30 mmol) are dissolved in 30 mL of water. pH is adjusted to 6.8 by addition of a solution of 1-deoxy-1-(methylamino)-D-glucitol (0.3 mL; 0.3 mmol), then MnCl₂ (30 mL; 30 mmol) is added in two hours, keeping pH at 6.8 by addition of 1-deoxy-1-(methylamino)-D-glucitol (28.2 mL; 28,2 mL). After 24 h the solution is filtered through a Millipore® (HA-0.22 μm) filter, nanofiltered, evaporated and the residue is dried on P₂O₅ to give the desired product (5,0 g; 14,65 mmol). The permeate containing the desired product is concentrated to 50 mL and the resulting solid (meglumine chloride) is filtered off. The solution is evaporated to a residue, which is crystallized from MeOH (50 mL) to yield 3 g of a second crop of the desired product (8,0 mmol).

Yield: 76%

¹H-NMR, ¹³C-NMR, IR and MS spectra are consistent with the structure.

What is claimed is:

1. A process for the preparation of compound (I), starting from octahydro-2a,4a,6a,8a-tetraazapentalen[1,6-cd]pentalene of formula (II), or from 1,2,3,4,6,7,8,9-octahydro-5H-4a,7,9a-triaza-2a-azoniacycloocta[cd]pentalene chloride of formula (IV), by formation of 1,4,7,10-tetraazabicyclo[8.1.1]tridecan-13-on-4,7-diacetic acid of formula (V), said process comprising the following steps represented in Scheme 2:

Scheme 2

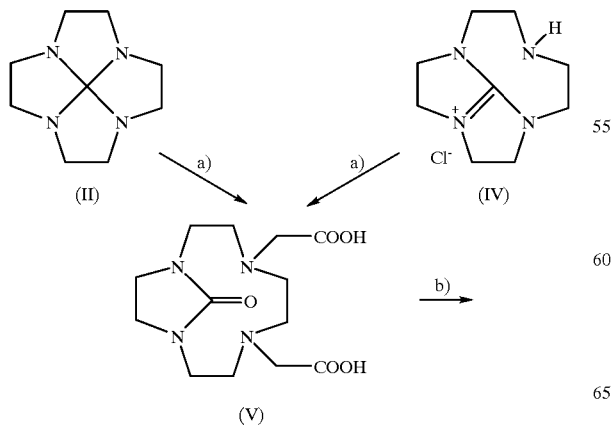

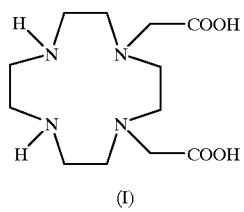

in which
step a) is an alkylation reaction in basic conditions with the alkylating agent XCH₂—COOH, in which X is a halogen;
step b) is a basic hydrolysis under pressure and at a temperature ranging from 150–220° C.

2. A process as claimed in claim 1 in which in step a) the reaction temperature ranges from 30 to 70° C.; pH ranges from 10 to 12 and the amount of alkylating agent is stoichiometric or up to 50% excess.

3. A process as claimed in claim 2, in which the alkylating agent used is BrCH₂COOH in a molar ratio of at least 2 mols per mol of starting product and in step a) temperature is 45° C. and pH is 11.5.

4. A process as claimed in claim 1, in which in step b) the basic hydrolysis is carried out in aqueous medium at basic pH by the addition of an amount of a base corresponding to 4–7 mols per mol of compound (V), at temperatures of 150–220° C.

5. A process as claimed in claim 4, in which temperature is 195° C. and pressure is 10 bar; and the base is added in an amount of 5 mols of NaOH per mol of compound (V).

6. 1,4,7,10-Tetraazabicyclo[8.2.1]tridecan-13-on-4,7-diacetic acid as an intermediate in the process according to claim 1.

7. A process for the preparation of a compound of formula (VIII), starting from compound (I), by alkylation with an excess of alkylating agent R—CH(X)—COY of formula (IX), optionally followed by reaction hydrolysis of the ester groups present, as shown in the following Scheme 3:

Scheme 3

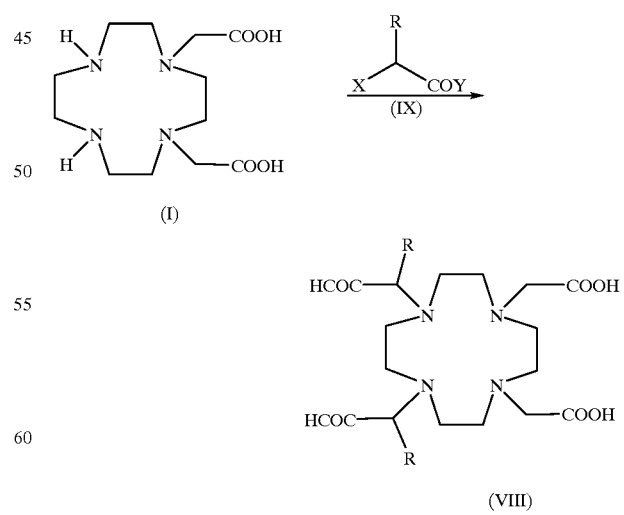

in which
R is a hydrogen atom, a straight or branched or cyclic C₁–C₆ alkyl group, unsubstituted or substituted or the alkyl group is interrupted by 1 to 10 oxygen atoms, or a $C_1$–$C_{20}$ alkyl group, optionally interrupted by a phenylene, phenylenoxy or phenylenedioxy group, in turn substituted by a straight or branched $C_1$–$C_6$ alkyl group unsubstituted or substituted by 1 to 7 hydroxy groups the phenylene group can be unsubstituted or substituted by alkoxy groups or by halogens, carboxy, carbamoyl, alkoxycarbonyl, sulfamoyl, hydroxyalkyl, amino, acylamino, acyl, or hydroxyacyl groups;

X is a halogen or a sulfonic acid reactive residue,

Y is a group —OH or —$OR_1$, wherein $R_1$ is a straight or branched $C_1$–$C_4$ alkyl group; when Y is —$OR_1$, the ester groups are subjected to a hydrolysis step, to obtain compounds (VIII).

8. A process as claimed in claim 7, in which the alkylating agent of formula (IX) is a compound R—CH(X)—COOH of formula (X), and X is bromine or chlorine.

9. A process as claimed in claim 8, in which the alkylating agent of formula (X) is a compound $XCH_2COOH$ of formula (XI), in which R is a hydrogen atom and X is bromine or chlorine.

10. A process according to claim 7, in which R is H or a straight or branched alkyl group in turn substituted by hydroxy groups or interrupted by oxygen atoms, as defined above; the phenylene group in R being selected from phenyl, benzyl, phenylmethoxymethyl;

$R_1$ is selected from the group consisting of methyl, ethyl, isopropyl, butyl, and tert-butyl;

X is selected from the group consisting of halogen a mesylate, benzenesulfonyloxy, nitrobenzenesulfonyloxy, tosylate and a triflate group.

11. A process as claimed in claim 10, in which the alkylating agent is 2-bromo-3-(phenylmethoxy)propanoic acid or 2-chloro-3-(phenylmethoxy)propanoic acid.

12. A process as claimed in claim 9, in which the alkylating agent of formula (XI) is selected from the group consisting of bromoacetic acid, 2-bromopropionic acid and 2-bromobutyric acid.

13. A process as claimed in claim 12 wherein α,α'-bis (methyl)-1,4,7,10-tetraazacyclododecane-1,4,7,10-tetraacetic acid is prepared.

14. A process as claimed in claim 11 wherein α,α'-bis [(phenylmethoxy)methyl]-1,4,7,10-tetraazacyclododecane-1,4,7,10-tetraacetic acid is prepared.

* * * * *